United States Patent [19]

Sarreal

[11] Patent Number: 5,684,226
[45] Date of Patent: Nov. 4, 1997

[54] MULTIPLE DISEASE RESISTANCE IN LETTUCE

[75] Inventor: Philip M. Sarreal, Monterey, Calif.

[73] Assignee: Harris Moran Seed Company, San Juan Bautista, Calif.

[21] Appl. No.: 483,649

[22] Filed: Jun. 7, 1995

Related U.S. Application Data

[63] Continuation-in-part of Ser. No. 178,076, Jan. 6, 1994, abandoned.

[51] Int. Cl.$^6$ .............................. A01H 5/00; A01H 5/10; A01H 1/04
[52] U.S. Cl. .................. 800/200; 800/255; 800/DIG. 13; 47/58
[58] Field of Search .................................. 800/200, 255, 800/DIG. 13; 47/58

[56] References Cited

U.S. PATENT DOCUMENTS 5,220,113  6/1993  Miltz ........................................ 800/200

OTHER PUBLICATIONS

Poehlmon. 1987. Breeding Field Crops. Third Edition. pp. 274–283.
Ryder. 1986. Lettuce Breeding. *In* Breeding Vegetable Crops. Bassett, ed. Ch. 12: 433–474.
Robinson et al. 1983. The Genes of Lettuce and Closely Related Species. Plant Breeding Reviews. 1: 267–294.
Kesseli et al. 1990. J. Cell Biochem. Suppl. O 14 Part E: 321. Abstract #R323.
Datnoff et al. 1989. Phytopathology. 79(10): 1190. Abstract #440.
Bos et al. 1990. Crop Protection. 9(1): 446–452.
Bonnier et al. 1992. Euphytica. 61:203–211.

*Primary Examiner*—David T. Fox
*Attorney, Agent, or Firm*—Townsend and Townsend and Crew LLP

[57] ABSTRACT

This invention provides for multiple pathogen resistant varieties of lettuce, *Lactuca sativa*. The varieties of this invention have a combined resistance to lettuce mosaic virus isolate Common, resistance to downy mildew pathotype I, resistance to corky root bacteria isolate CA1, *Sclerotinia minor* and resistance to big vein disease via infection through *Olpidium brassicae*. The varieties having a non-albino phenotype, a average mature head of 15 cm diameter and are male fertile. The varieties are developed through selective breeding.

9 Claims, No Drawings

MULTIPLE DISEASE RESISTANCE IN LETTUCE

This is a FWC Continuation-in-Part of application Ser. No. 08/178,076 filed Jan. 6, 1994, now abandoned.

BACKGROUND OF THE INVENTION

FIELD OF THE INVENTION

This invention provides for multiple pathogen resistant varieties of lettuce, *Lactuca sativa*. The varieties are developed through selective breeding.

There is a continual need for improved lettuce varieties. This invention teaches and provides for lettuce plants that have resistance to five major lettuce diseases: Sclerotinia disease, downy mildew, lettuce mosaic, corky root and big vein. Each of these had been, for the past 50 years of the coastal lettuce industry, a major disease at one time or another, with significant economic losses. The introduction of multiple disease resistances into the germplasm of lettuce is a significant improvement in the germplasm. Never before have five distinct and commercially important disease resistances been combined into a single lettuce variety.

SUMMARY OF THE INVENTION

This invention provides for novel varieties of Lactuca sativa having resistance to *Sclerotinia sclerotiorum*, lettuce mosaic virus isolate Common, resistance to downy mildew pathotype I, resistance to corky root bacteria isolate CA1 and resistance to big vein disease via infection through *Olpidium brassicae*. The varieties have a non-albino phenotype, an average mature head of 15 cm and are male fertile. It is especially desired that the varieties have green leaf types. The mature heads have an average diameter mature head of about 15 cm and weigh about 900 grams. A suitable maturity rate is also desired. A preferred maturation rate is one where the average mature head is reached in less than about 85 days when grown under optimal soil conditions and daily average temperature of 65° F. in full sun of twelve to thirteen hours duration. It is preferred that the average mature head is reached in less than 70 days.

The color of the leaves is preferably a dark green that is between RHS of 146A and 146C. The leaves preferably have a smooth margin. The seeds may be white.

DEFINITIONS

"Average mature head" refers to the mean size of 20 heads which have reached their largest marketable size prior to bolting under growing conditions where nutrition, light and temperature are not rate limiting.

"Male fertile" refers to a lettuce variety that produces viable pollen.

"Non-albino phenotype" refers to a lettuce variety which produced normal levels of chlorophyll and can survive without addition of a carbon source. The leaf type can be green or red. Albino leaves are typically white.

"Optimal soil conditions" refers to soil conditions where nutritional requirements are not rate limiting to the growth of the plant.

"Resistant" refers to a plant that exhibits no symptoms or insignificant symptoms. Significant symptoms are those that affect marketability such as appearance of the lettuce head. An occasional necrotic lesion would be an example of a insignificant symptom. It would be understood that the pathogens responsible for the five named diseases may be present in significant numbers but are not inducing symptoms.

"Resistance to big vein disease via infection through *Olpidium brassicae*" refers to a level of resistance in a novel lettuce variety as measured by visual symptoms. Resistance is deemed present when symptoms are not present in at least 85% of the novel variety plants when compared to a known resistant lettuce variety growing under comparable conditions to the novel variety.

"Resistance to corky root bacteria isolate CA1" refers to a level of resistance in which no visual symptoms are present on the roots of the novel variety under conditions in which susceptible varieties demonstrate at least 80% infection.

"Resistance to downy mildew pathotype I" refers to a level of resistance in which no mycelium or sporulating structures are visible to the naked eye under conditions which do give rise to this level of fungal growth compared to the susceptible varieties identified herein.

"Resistance to lettuce mosaic virus isolate Common" refers to resistance to LMV isolate Common when measured by visual symptoms. A variety is considered resistant when no visual symptoms are present in comparison to a known susceptible variety of lettuce as identified herein.

"Resistance to Sclerotinia minor" refers resistance to leaf drop of lettuce or lettuce drop. A variety is considered resistant when greater than 80% of a variety is not visibly infected in a field harboring *S. minor* under weather conditions in which susceptible varieties, i.e. SALINAS exhibit about 90% infection.

"RHS" refers to the Royal Horticulture Society of England which publishes an official botanical color chart quantitatively identifying colors according a defined numbering scheme. The chart may be purchased from Royal Hort Society Enterprise Ltd RHS Garden; Wisley, Woking; Surrey GU236QB, UK.

DETAILED DESCRIPTION OF THE INVENTION

This invention provides novel lettuce varieties having a multiple gene-based, multiple pathogen resistant phenotype against five common lettuce diseases. The diseases are downy mildew, corky root rot, lettuce mosaic virus, sclerotinia disease and big vein of lettuce. The successful crossing of lettuce varieties may be hampered by a number of problems. Prior to this work, it was not known whether the five specified disease resistances could be combined in a commercially viable lettuce variety. Common problems include dwarfing, albinoism and male sterility. The following text details methods for the successful introduction of these multigene based pathogen-resistance factors into lettuce.

Any variety of *Lactuca sativa* may be used as starting material. The resistant lines are selected from individuals that are first crossed to produce as an F1 generation. The parental varieties are preferably selected from commercial varieties that individually exhibit one or two of the resistant phenotypes that are desired in the new variety. For the convenience of those wishing to develop novel lines of multiply pathogen resistant lettuce varieties, variety HMX 2557 has been deposited according to the terms of the Budapest Treaty with the American Type Culture Collection (ATCC) of 12301 Parklawn Dr.; Rockville, Md. U.S.A. on Jan. 23, 1997, and assigned ATCC Designation No. 97855. HMX 2557 is a preferred parental line carrying the five disease resistances recited herein. This variety can be crossed with other conventional lettuce varieties in accordance with this invention.

To optimize crossing, it is important to note that lettuce is an obligate self-pollinating species. This means that the pollen is shed before stigma emergence, assuring 100% self-fertilization. Since each lettuce flower is an aggregate of about 10–20 individual florets (typical of the Compositae family), manual removal of the anther tubes containing the pollen is tedious. As such, a modified method of misting to wash the pollen off prior to fertilization is needed to assure crossing or hybridization.

About 60–90 min past sunrise, flowers to be used for crossings are selected. The basis for selection are open flowers, with the stigma emerged and the pollen visibly attached to the single stigma (about 10–20 stigma). Using 3–4 pumps of water from a regular spray bottle, the pollen are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers.

About 2–3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching the methods for out crossing lettuce are: (1) Ryder, E. J. and A. S. Johnson. 1974. Mist depollination of lettuce flowers. *Hortscience* 9:584; and (2) Nagata, R. T. 1992. Clip and Wash Method of Emasculation for Lettuce. *Hortscience* 27(8):907–908.

The progeny of these crosses are screened according to the methods described below. The initial screenings can be for any of the five diseases. It is optionally efficient to screen for more than one disease simultaneously. For example in the Examples provided, two sets of lettuce seedlings, both starting at the $F_2$ generation are screened simultaneously for downy mildew and for corky root rot. Each successful cross is optionally followed by selfing for approximately six generations to ensure that the desired traits are suitably fixed in the population.

The five lettuce pathogens to which this invention is directed are well recognized as distinct pathogens. The pathogen causing downy mildew in lettuce is *Bremia lactucae*. Any of the following pathotypes are useful as screening agents: pathotypes I, II, IIB, III and IV. *B. lactucae* is an obligate parasite. Its conidiophores are rigid and hyaline, usually 1–3 arising from a lettuce stomata, usually slightly constricted between the guard cells. Dichotomous branches (3–7) give the conidiophore a tapering appearance. Septa are found in the main trunk and branches. Branch tips swollen into an inverted cone or drum shape vesicle. The vesicle usually bears 3–5 sterigmata which narrow to a point and bear a conidium.

The conidia are spherical to ovoid (length 12–32 µm, 1.5–2 µm diam.), hyaline, pedicel up to 2 µm, apical papilla has slightly thickened wall. The organism is biotropic and grows through the host by means of variable, intercellular, coenocytic hyphae. Haustoria are irregular but frequently saccate-clavate, about 16 µm long. Oospores are infrequently found in intercellular spaces in host tissue.

The macroscopic signs are clearly evident in plants exhibiting heavy sporulation. The leaf surfaces exhibit a finely densed to loosely scattered with furry mat of conidiophores, usually on the lower surface of leaves under chlorotic or partially necrotic lesions.

*B. letucae* is an obligate parasite and is not available from the ATCC. It is typically found growing wild on the wild lettuce (*L. serriola*) commonly found growing in California especially Monterey county. It is conveniently available from Dr. Richard Michelmore; UC-Davis from whom one can acquire any pathotype (ie. I, II, III, IV, and IIB, as well as some novel races). Pathotypes are identified by their relative ability to infect various known differentiating varieties of lettuce. Using the gene for gene theory of resistance, it is believed that for the 5 identified pathotypes (I, II, IIB, III and IV) there are at least 18 distinct genes of resistance. They are described, e.g., Dm 5/8 for pathotype I, Dm 4 against pathotype IIB and Dm 10 against pathotype III. The most common pathotype is III and it is identified by its ability to infect plants having the Dm 5/8 allele (as in Var. SALINAS) and its inability to infect plant carrying Dm 10 (as in Var. VANGUARD). A general reference describing this pathogenicity is Ilott, T. et al., 1987, Genetics of Virulence in California Populations of *Bremia Lactucae*, *Phytopathology*, 77(10):1381–1386.

The $F_2$ lettuce generation is screened for resistance to downy mildew in comparison to standard varieties. Comparative resistance can be viewed by using resistant strains such as Var. ALPHA DMR from Harris Moran or public varieties such as UC 206 as resistant controls and Var. SALINAS as susceptible controls. The seeds are sown in compartmented boxes according to the downy mildew screening procedure of Example 3 and grown in refrigerated chambers. Susceptibility is determined by overt growth of the fungus on the lettuce leaves.

The pathogen responsible for corky root is *Rhizomonas suberifaciens*. CA1 is the most common strain and is publicly available from the ATCC (Accession No. 49355). Other useful strains include CA3 and CA15. Colonies of *R. suberifaciens* are initially translucent but later become opaque. The colonies are umbonate, compact colonies, which ultimately become wrinkled and have raised edges on S-medium as described in Van Bruggen, et al. 1990, Host Range of *Rhizomonas suberifaciens*, the causal agent of corky root of lettuce. *Plant Disease*, 74:581–584.

*R. suberifaciens* is an aerobic bacterium, ranging in morphology from small (0.6–1.4µ by 0.3–0.6µ) rods with one lateral flagellum to long filaments. According to the KOH stringiness test, the bacteria seemed gram-positive, but with Hucker's gram-stain the bacteria stain gram-negative.

The type strain CA1 and other equivalent strains are publicly available in the Salinas Valley of California growing in the soil of the lettuce fields. It is quite common and can be isolated using the baiting procedure described in Example 4 and characterized strains are conveniently available from Dr. Ariena Van Bruggen at the University of California at Davis.

An initial screen for corky root is initiated using the screening procedure of Example 4. The seeds are sown under greenhouse controlled conditions in vermiculite soil with a heavy concentration (approx. $10^7$ cfu/ml) of corky root bacteria. The screening for downy mildew resistance can also be done from the corky-root resistant seedlings, either at the stand establishment stage or a month after transplanting through leaf disk method. The secondary screening for downy mildew resistant plants among corky root resistance selected plants needs to done on newly-germinated seedlings. Thus the downy mildew resistant plants are allowed to mature and their progeny screened for resistance to corky root. Susceptibility is determined by visually inspecting the tap roots for yellow to golden oblong lesions. Advanced symptoms include a brown to golden root system and a corky and brown tap root.

The major pathogenic race or pathotype of corky root is CA1 but other strains are known. The cor gene is recognized as the single gene responsible for resistance.

The third pathogen is a potyvirus known as Lettuce mosaic virus (LMV). Natural transmission of LMV is achieved by the green peach aphid (*Myzus persicae*) feeding on infected host leaves (wild lettuce and bristly ox-tongue are the two most important natural hosts). The virus is non-persistent in the aphid and seed-borne. The common strain is available from the ATCC. The ATCC accession number is PV-63. Infected leaf tissue can be conveniently stored in the freezer at $-20°$ C.

While the order for assaying for pathogen resistance is not critical, the assaying for LMV after identification of resistance of downy mildew or corky root is convenient. Individual single plant selections showing resistance to either downy mildew or corky root as defined by Examples 3 and 4 respectively are then inoculated with lettuce mosaic virus [LMV] according to Example 5. In brief, the virus or ground leaves infected with LMV are mixed with a buffered solution and abraded with carborundum or sand onto the leaf surfaces of the test plants. Inoculation with LMV is at stand establishment when the plants have recovered from the previous screening. Stand establishment is about 3-4 weeks after transplanting, when the plants present two or three expanded leaves. Waiting until stand establishment increases the efficiency of screening for viral-induced mosaic symptoms.

Resistance to LMV is considered under the control of a single recessive gene. Resistant varieties are publicly available as described in Example 5 and can be used as starting material for introducing resistance to LMV into novel lettuce varieties.

The fourth pathogen is *Sclerotinia minor*. *S. minor* is a primary etiologic agent of leaf drop of lettuce. The disease and pathogen were described in the first quarter of this century. Beach W. S. 1921, The lettuce 'drop' due to S. *Sclerotinia minor*, PA Agric. Exp. Stn. Bull 165:16–23.

Lettuce drop is a very destructive and widespread disease. It is the predominant pathogen in the San Jaoquin and Salinas Valleys in fields in which lettuce is regularly cultivated. It attacks early in either of the spring or fall seasons for growing lettuce. The soil-borne sclerotia directly infect the roots, crown and leaves on or near the surface by the eruptic myceliogenic germinatino where a mas of hyphae emerge from the sclerotium. The infection is initiated on senescent or injured tissues, usually on lower senescing leaves. The symptoms typically manifest near maturity. Diseased plants rapidly wilt and yellow either totally or in the larger more mature leaves. The basal portion of the plant are usually decayed. The disease is favored by cool wet weather common in coastal regions where lettuce is commercially grown. The pathogen is viable in the soil for 2-3 years. *S. minor* which is predominant in the coastal area of northern California is distinguished from *S. sclerotiorum* by the later having bigger sclerotial bodies (hard, black reproductive bodies). A review of lettuce drop can be found in Patterson and Grogan, 1984, Cause and Control of Lettuce Drop in California, UC Davis Publication and in Patterson and Grogan, 1985, Differences in Epidemiology and Control of Lettuce Drop caused by *S. minor* and *S. sclerotiorum*, Plant Disease, 69(9):766–770.

None of the parents used in the crosses exhibited resistance to *S. minor*. The progenies were developed in fields that were naturally infected and weather conditions created ideal conditions for the disease. Resistance to lettuce drop was a surprise.

Susceptibility to *Sclerotinia minor* is determined by field conditions. There is no accepted laboratory assay. *S. minor* is endemic in the Salinas Valley, Calif. and suitable farms include: (1) the Harden Ranch 2, Fontes Farms (off Boronda Rd.), Salinas, Calif.; (2) D'Arrigo Farms, Block 26, Ranch 11 (off Ft. Romie Rd) Soledad; and, (3) D'Arrigo Farms, Blanco Rd, Salinas, Calif. With exception of the described varieties, there are no known lettuce varieties with resistance as described here.

In general, one determines resistance by growing the test variety against known susceptible varieties. There are no known lettuce varieties with the degree of resistance described herein. Field conditions for testing must be either early spring or fall (in California, March or September plantings) when humidity in the morning is 100% and the average temperature is between $55°–65°$ F. The test plots are made as equivalent as possible using standard field plotting techniques and resistance is defined by a visible infection. The symptoms are rotting or decaying basal portions of the plant. There is no practical survival or partial infection to provide a relative scoring. The plants are either infected and die or not infected. A 75% to 80% suvival rate marked a variety as resistant or tolerant while susceptible varieties such as MONTELLO or SALINAS have only a 10% resistance under similar field conditions.

The fifth pathogen of lettuce is lettuce big vein disease. The causal agent of lettuce big vein disease is a viral agent transmitted by a soil-born fungus *Olpidium brassicae*. The viral agent has not yet been purified and characterized; but, it is a recognized viral disease. Plant and soil samples are collected from big-vein infected fields in Salinas, Calif. and Yuma, Ariz. The soil-borne fungus *Olpidium brassicae* and the symbiotic virus is widely distributed on most if not all the lettuce farms in the Salinas Valley. Suitable locations include: (1) Harden Ranch 2, Fontes Farms (off Boronda Rd.), Salinas, Calif.; (2) D'Arrigo Farms, Block 26, Ranch 11 (off Ft. Romie Rd) Soledad, Calif.; (3) Spruce Canal Gate #21 (east of Kalin Rd), El Centro, Calif.; (4) Bruce Church Farms, Lot 204.2, off Laguna Dam Rd., Gila Valley, Yuma, Ariz.; (5) Nakasawa Ranch, off Laguna Dam Rd, Gila Valley, Yuma, Ariz.; (6) Elder Canal Gate 127 (Forrester Rd and Wienert), Brawley, Calif.; (7) D'Arrigo Farms, Ranch 17 (off Abbott St), Soledad, Calif.; and (8) Bruce Church Farms, NW corner of Ross Rd and Fisher, Bard, Calif.

To ensure that the soils are truly infected, Olpidium may be propagated and tested in plants of lettuce Var. Climax grown in sand culture. Zoospore suspensions are prepared by washing the roots free from sand and immersing them in tap water. Drops of water are then removed and examined with a phase-contrast or dark-field microscope for motile zoospores and population counts are taken. The plants are then surveyed for symptoms diagnostic for big vein disease.

For convenience the test plants are typically grown in infected soils and surveyed for resistance within a few weeks of germination as described below in Example 6. The genetic basis for resistance to big vein disease is not definitively characterized. The sensitivity of the resistance to environmental factors implies that the genetic basis for resistance involves more than one gene.

To facilitate screenings, the selected, resistant seedlings from both the corky root and downy mildew screenings are transplanted at big-vein infected grounds according to Example 5 and are simultaneously tested for resistance to LMV. Selections for resistant lines for lettuce mosaic virus will show up in three weeks.

Following this procedure, three groups of multiple resistant lines were developed for the different growing slots (planting times) of coastal California. It should be noted that while the California coastal areas (Salinas and Santa Maria areas primarily) have a relatively mild weather patterns (daily mean temperature range of 52° F. in the winter to 63° F. in the summer, daylength range of 10–14 hrs during the growing season), distinct microclimates are found throughout the valleys during the growing season (January–November, with a two-week, lettuce-free period in December at Salinas). As such, head size becomes critical for the three planting slots.

The following examples are provided by way of illustration only and not by way of limitation. Those of skill will readily recognize a variety of noncritical parameters which could be changed or modified to yield essentially similar results. Unless otherwise stated all varieties are publicly available through a variety of common sources.

EXAMPLES

Example 1

Producing a multiple pathogen resistant lettuce.

Several new varieties of lettuce having resistance to all five pathogens of lettuce were developed from the original cross initiated at Cornell University (Ithaca, N.Y.) in 1980. These parental lines involved the varieties ITHACA (an eastern type lettuce—yellow green leaves, frilly margin, very spiralling, compact heads—with resistance to broad bean wilt virus), and VANGUARD 75 (a dark green, large-framed, mosaic resistant lettuce for the California and Arizona desert winter planting). Selected progeny from the cross were later crossed with MONTELLO (another eastern type lettuce with resistance to corky root rot disease). None of the parents were resistant to S. minor.

The resulting progeny from the latter cross were highly segregating, i.e., the population was not very uniform with regards to type (color, leaf margin, leaf texture) and disease resistance. These plants were screened for resistance at Harris Moran (HM) as described below in Examples 4 and 5. The successful crosses were selfed for 6 generations selecting for optimal plants for both pathogen resistance and commercially acceptable growth habits. The sixth generation was then crossed with PACIFIC, a variety known to be resistant to big vein disease and to downy mildew pathotype I.

Screenings for LMV, corky root, downy mildew and big vein disease lead to the selection of stably inherited multiply resistant lettuce lines which were designated HMX 2553, 2554, 2556, 2557 (PREMIERE), 2558, 2559 and 2560. HMX 2560 has a small frame; 2553 and 2554 have a medium frame; 2556-9 are larger framed lines. They are all specifically adapted for the California coastal growing seasons as described above with 2556 and 2557 showing exceptional resistance to S. minor.

Example 2

Transferring multiple resistance to commercial lettuce varieties.

Using the varieties identified in Example 1 as 2558 (glossy, lighter green leaves) as a donor male plant, with Alpha DMR (dull, dark green leaves) as the female recipient lettuce variety, the pollen is removed from Alpha and crosses are made by introducing the pollen from 2558. The F1 seeds are grown and identified (by leaf color and texture); the maternal plants (those exhibiting characteristics exactly like Alpha and none of 2558) are selected out. A total of 10–15 F1 plants are then selfed and allowed to have seeds. The harvested seeds ($F_2$ generation) are planted and screened for downy mildew, corky root, lettuce mosaic and corky root following procedures described herein. Those plants exhibiting resistance to all five diseases are retained and further screened for stability and marketable traits.

Example 3

Screening for Downy Mildew.

As described above, the pathogen causing downy mildew in lettuce is *Bremia lactucae*. The pathogen does not store well apart from host tissue. Principal method of storage is on a universal susceptible type of lettuce (Dark Green Boston, DGB). For cryo-storage at −85° C., 1 ml (in a 2 ml vial) of the spore suspension can be used for inoculations or lift blotter paper with sporulating seedlings (7 days after inoculation) and place in a deep glass petri plate and wrap with electrical tape instead of parafilm and freeze. To remove spores from cryo, gradually thaw the vial by placing it in a −20° C. freezer for a few hours then into an ice bath for a few more hours before spraying seedlings.

To increase the inoculum of *B. letucae*, one inoculates on a susceptible lettuce host such as public Var. Dark Green Boston [DGB]. Typically pathotypes which are being used a lot for continuous screening need to have 2–3 plastic boxes (W×L×H=21×32×5 cm) of DGB planted and inoculated with the appropriate pathotype. Seven plastic boxes bearing plants with heavy sporulation is enough to spray 15 tool boxes (W×L×H=16×26×4 cm) plus seven plastic boxes of DGB.

Plastic boxes (used for inoculum increase) and tool boxes sectioned into 18, 4×4×5 cm squares per box are used for screening of breeding lines and are used for seeding of lettuce. Containers are thoroughly washed and wiped out with 70% alcohol before each use. Two layers of filter paper are placed in each box or square compartment. The plastic boxes are treated with Hewitt's or ½ strength Hoagland's solution until the filter paper is saturated. For tool boxes, about 5 ml of Hewitt's or ½ strength Hoagland's solution/square. The compositions for Hewitt's and Hoagland's solutions are described respectively in: Hewitt, 1952, Sand and Water Culture Methods Used in the Study of Plant Nutrition, Tech Comm. Commonwealth Bureau of Hort and Plantation Crops, East Mailing, Maidstone, Kent and Hoagland and Avon, 1950, California Agric. Exp. Circ. No. 347.

Roughly 25 lettuce seeds/square and 300–400 seeds per plastic box are randomly sprinkled into place. The seeds are germinated in a room with a temperature of 24°–26° C. with 16 hrs of high intensity fluorescent lighting. The boxes are checked every second day, and additional Hewitt's or Hoagland's solution is added as needed.

Lettuce seedlings are inoculated at six days. The cotyledons should be open and expanded. The ideal time to inoculate seedlings is when the first true leaf is emerging.

To obtain inoculum, remove sporulating seedlings from the plastic boxes and place them in a 1000-ml glass beaker. Wash the spores off the seedlings with cold distilled water. Decant into 50 ml centrifuge tubes. Centrifuge for 8–10 minutes at 3,000 rpm. Siphon off down to 5 ml depending on the spore load. Combine all concentrated spores and dilute until there is a volume of 30–40 ml of inoculum.

To inoculate test seedlings use a concentration of $1 \times 10^4$ spores/ml. Mist approximately 0.25 ml/square (approx. two quick sprays) within a tool box using an atomizer sprayer (available from Sigma Laboratories, St. Louis, Mo.) or its equivalent.

If working with more than one pathotype, extra care should be taken to avoid cross contamination by spraying alcohol on equipment, work area and hands between each different pathotype. Work should also be performed in a transfer hood. Different spray heads should be used for the different pathotypes. Always run alcohol through the spray heads after each use. Spray the tool boxes before spraying the boxes. A forceful mist could kill the spores.

The boxes of freshly inoculated seedlings are placed in an incubator with the following conditions: a constant temperature of 15° C., with 10 hrs. of light. Reading of test plants can be made at 10 days after inoculation. Plants exhibiting little or no sporulation at 10 days should be kept for another 2–4 days for the final reading. Seedlings are rated as either resistant or susceptible based on visible inspection. Resistant individuals are identified by either no sporulation or by hypersensitive spots. Each line being tested is replicated at least two times. Replications should be located in different tool boxes.

Positive and negative controls are used to provide comparisons. DGB is used as a susceptible check for all pathotypes. Lettuce Var. ALPHA is used as a resistant variety check to all pathotypes except for 2B. Lettuce Var. SALINAS can be used as a resistant check for pathotype I and Var. TARGET from Peto Seeds can be used as a susceptible check for type II. UC 206 is a resistant control for pathotype IIB and EL TORO or VANGUARD are used as resistant controls for pathotype 3. Checks should be included in each tool box planted.

Older plants can be tested for downy mildew. This is accomplished by placing plants within a plastic bag and inoculating with spores of *B. lettucae*. The bag is sealed with a twist tie and place in the incubator as described above. Results are read in 14 days. Alternatively screening can be done by planting lettuce in seedling flats. The plants are grown to produce a few leaves, are spray inoculated and place in a humidity chamber in the greenhouse (maintained at 65°–70° F.) for 7–10 days.

The leaf disk technique is an alternative method to confirm results found with the seedling test using older leaves. Mature leaves are removed from plants and are washed with distilled water. Circles (5–10) are then cut out of the leaves with a cork borer (#15). Leaf disks are then placed bottom side up in a plastic box containing blotter paper saturated with Hoagland's solution. The disks are inoculated and incubated in the same manner as the seedling test.

Suitable references discussing this disease include: Michelmore, R. and I. R. Crute. 1982. A Method for Determining the virulence Phenotype of *Bremia lactucae* Isolates. *Trans. Br. Mycol. Soc.* 79(3): 542–546 and Ilott, T. W., et al. 1987. Genetics of virulence in California populations of *Bremia lactucae* (lettuce downy mildew) *Phytopathology* 77: 1381–1386.

Example 4

Corky Root Inoculation Techniques.

The pathogen responsible for corky root is *Rhizomonas suberifaciens*. CA1 is the most common strain, other useful strains include CA3 and CA15. Colonies of *R. suberifaciens* are initially translucent but later become opaque. The colonies are umbonate, compact colonies, which ultimately become wrinkled and have raised edges on S-medium. S-medium is described in Van Bruggen, A. H. C., et al. 1990. *Plant Disease*. 74(8):581–584.

*R. suberifaciens* is an aerobic bacterium, ranging in morphology from small (0.6–1.4μ by 0.3–0.6μ) rods with one lateral flagellum to long filaments. According to the KOH stringiness test, the bacteria seemed gram-positive, but with Hucker's gram-stain the bacteria stain gram-negative.

The type strain CA1 and other equivalent strains are publicly available in the Salinas Valley of California growing in the soil of the lettuce fields. Using soil samples, the organism can be isolated by using 2–3 week old seedling of a susceptible variety like SALINAS as baits. Soil suspensions are made by using 50 g of soil in 75 ml of distilled water plus 3 drops of Tween™ 20. The suspensions are stirred for 10–20 minutes and filtered through six layers of cheesecloth. Suspension (5 ml) is dispensed at the base of each of five 2–3 week old seedlings in a greenhouse. Three-four weeks after inoculation, the plants are uprooted and the bacteria is isolated from the yellow or corked areas on the roots.

Root samples are rinsed under running tap water, sonicated in 20 ml of sterile distilled water, and comminuted in a sterile mortar with 10 ml of sterile distilled water. The cell suspensions obtained from the root surface by sonication and from comminuted roots are filtered through a 65 μm sterile filter, and 0.04 ml of filtered suspension (undiluted and 10-fold diluted) is spread into plates of S-medium amended with streptomycin sulfate. The plates are incubated at 28° C. for 10 days. The slow-growing colonies of the CR bacteria are identified by their translucent, later opaque colonies in S-medium. The most well studied strains may be obtained from Dr. Ariena Van Bruggen at the University of California at Davis.

Bacterial cultures are stored long term at −85° C. A 72-hour liquid culture in S-medium is diluted to 15% glycerol. The cultures are slightly unstable after successive transfers on solid S-medium and pathogenicity may be affected.

To increase the inoculum for screening, one cryovial is thawed and added to 10 ml liquid S-medium. The medium is left at room temperature with continual shaking for 4 days. *R. suberifaciens* is not a vigorous growing bacteria. If growth is heavy after 2 days, then there is a strong likelihood of contamination. The original 10 ml is used to seed larger volumes of liquid S-medium at the rate of 1 ml:1 liter. To check for contaminants, streak 1 loop onto a plate of S-medium and CS-20. *R. suberifaciens* does not grow well on CS-20. After 3–4 days at room temp. there will be distinct colonies on S-medium. After 5–6 days of continual agitation/shaking at room temperature, the cultures will be cloudy and turbid. The cultures are then diluted 50% with deionized, distilled water.

The diluted culture media is applied to 1020 trays of 7-day old seedlings at a rate of at least 500 ml per tray. Any excess water in the trays is removed prior to inoculation by sifting in the tray before adding inoculum.

Resistant varieties of lettuce are available and include commonly available varieties such as GREENLAKE, MONTELLO, SOUTHBAY, RALEIGH, MISTY DAY and GLACIER. Susceptible varieties are also commonly available and include SALINAS.

The screening of lettuce seedlings conveniently takes place in K36D1 cell inserts in a no. 1020 Tray without holes. The tray combinations are available from Kord Products, Ltd. Bramaton, Ontario, Canada. 10–20 Seeds are sown per cell in vermiculite. The seedlings are kept at 17°–28° C. throughout the test with 14 hr of light. The trays are misted daily for at least 2 weeks and/or watered from below by adding about 1 cm of water to the tray. Between waterings, the tray is allowed to become dry, yet the vermiculite should remain moist.

Approximately 10 days after sowing, the flats are flooded with half-strength Hoaglands solution to supply nutrition. The seedlings are watered every other week with 0.005M $CA(NO_3)_2$+0.005M $KNO_3$.

The seedlings are inoculated with the bacteria approximately 7–8 days after sowing. The preferred time is when the root system has started to expand. The liquid in the bottom of tray is removed and inoculum is added to a depth of 1 cm. The seedlings are not watered for at least 24 hours. The trays may be misted. A second inoculation is done 2 weeks later.

Post inoculation, the seedlings are maintained as they were during the growth phase. The flats are kept moist with a maximum of 1 cm of water in the tray. The trays may be allowed to go dry; however, the vermiculite must remain wet at all times.

Susceptibility to corky root is presented by plant stunting and poorly developed root systems. The tap root develops yellow to golden oblong lesions, especially where the lateral root has emerged. The entire root system is brown to golden and in advanced cases, the tap root is corky and brown. The absence of stunting, and lesions under the conditions provided is evidence of resistance. The duration of test from sowing to reading is approximately 4 weeks.

Suitable references are Van Bruggen, et al. 1990. Host range of *Rhizomonas suberifaciens*, the causal agent of corky root of lettuce. *Plant Disease.* 74(8):581–584; Van Bruggen et al. 1990. The Effect of Cover Crops and Fertilization with Ammonium Nitrate on Corky Root of Lettuce. *Plant Disease.* 74(8):584–589; and, Van Bruggen et al. 1990. Distinction between Infectious and Non-infectious Corky Root of Lettuce in Relation to Nitrogen Fertilizer. *J Amer Soc. Hort Sci.* 115(5):762–770

Example 5

Screening for Lettuce Mosaic Virus.

Resistance to lettuce mosaic virus (LMV) is determined using a standard, mechanical inoculation. Three to four weeks prior to inoculation of test plants or breeding lines, the virus is increased by inoculation on susceptible lettuce varieties like GREEN TOWERS, SALINAS and VANGUARD. Resistant checks can be done using varieties DON JUAN, SALINAS 88 AND VANGUARD 75. The infected leaves are then ground in a buffer solution of 0.5M potassium phosphate ($K_2HPO_4$, 8.71 g/l) at pH 7.2 in a ratio of 1 g leaf to 4 ml buffer solution. An antioxidant (mercaptoehanol)is also added, as well as activated charcoal at 0.25 g. Carborundum at 0.4 g can be added to the inoculum, then rubbed to the leaves of test plants.

The test plants include both seedlings and mature plants. Seedlings selected from downy mildew screens are very small (cotyledon stage) and sensitive to abrasion. They are transplanted in flats till they recovered to their 3–4 leaf stage, when they are inoculated. The seedlings from corky root screens are bigger, being 4–5 weeks old, but have bare roots. They are transplanted into flats and after about two weeks are fully recovered.

About three weeks after inoculation, plants showing symptoms are culled out, and the remaining plants grown till the flag leaf stage, when they are rated again for mottling symptoms. Plants are either fully resistant or designated susceptible.

Suitable references include: Pink, D. A., et al. 1992. Differentiation of pathotypes of lettuce mosaic virus. *Plant Pathology.* 41:5–12; and, Ryder, E. J. 1973. Seed Transmission of Lettuce Mosaic Virus in mosaic resistant lettuce. *J Amer Soc Hort Sci.* 98(6):610–164.

Example 6

Screening for Resistance to *S. minor.*

Test varieties of lettuce are screened for resistance to *S. minor* by field testing of test varieties against varieties of known susceptibility. Resistance is defined as 75 to 80% survival under field conditions where susceptible varieties have only 10% survival rates.

Suitable fields include any farm plots in the Salinas Valley, California where lettuce has been previously cultivated in the last two years. Examples of suitable farms are provided above. Plantings are made during September or March when weather conditions are most likely to produce heavy infections of *S. minor.*

Testing of resistance versus susceptibility is done by visible screening for death due to rapid wilt and decay at the ground level or basal portion of the plant.

Ratings are done based on percentage of infected plants, relative to the controls. The infections are scored either plus or minus. There are no relative scores of infection degree. More specifically, the newly bred plants or varieties are tested in side by side growing trials using Var. SALINAS as a control because it has a relative susceptibility of 80% when grown under optimum conditions for the organism. A successful conferring of genetic resistance is evident when the plants are greater than 80% resistant to leaf drop due to *S. minor.*

Example 7

Screening for Lettuce Big Vein Disease

Test varieties of lettuce are screened for resistance to Lettuce big vein disease by sowing 30–40 seeds of each breeding test line in a fine sand potting mix in 100-ml plastic cup, and maintained in growth chamber at 13° C. minimum. One week after planting, each cup is inoculated with $1 \times 10^6$ big vein infected zoospores of Olpidium. Plants are then fertilized twice a week with ½ strength Hewitt's solution one week after inoculation. After 3–4 weeks at 16°–18° C., vein-banding symptoms start showing. The length of the latent period for big-vein symptom development can be shortened by larger number of zoospores in the inoculum. Ratings are done as to severity of symptom expression and resistant plants (those not showing symptoms) are selected and transplanted.

Variabilities in symptom expression are commonly observed in plants. Severe symptoms had been associated with cool temperatures (16°–18° C.) when both roots and tops of the plants are kept at the same temperature.

Optionally, resistance to big vein disease is done in both laboratory tests and in field trials. With regards to field transplanting for corky root and downy mildew selections in big-vein prone soils, transplanting is done during February--March at San Juan Bautista, Calif. Indexing for field resistance is done at Salinas, Calif. (sowing January–February); 2and El Centro, Calif. and Yuma, Ariz. (sowing in October–November), where direct seeding is done in 25-ft long bed (double rows). The beds are thinned to a stand of 50–60 plants per bed, replicated 2–3 times. Susceptible varieties SALINAS or VANGUARD, and resistant variety PACIFIC are included as controls. Growers have observed that big-vein symptoms are more severe in Imperial Valley and Yuma than in the Salinas Valley.

Ratings are done based on percentage of infected plants, relative to the controls. More specifically, the newly bred plants are tested in side by side growing trials using Var. PACIFIC as a control because it has a relative resistance of 85% when grown under optimum conditions. A successful conferring of genetic resistance is evident when the plants are 85% resistant to big vein disease. Susceptibility is determined by visual identification of any one of the following symptoms, vein clearing, mottling of the leaves or stunting.

Suitable references include Campbell, R. N. et al. 1980. Big Vein of Lettuce: Infection and Methods of Control. *Phytopathology.* 70(8):741–746; Westerlund, F. et al. 1978. Effect of Temperature on Transmission, Translocation and Persistence of the Lettuce Big Vein Agent and Big-Vein Symptom Expression. *Phytopathology.* 68(8): 921–926; and Westerlund, F. et al. 1978. Soil Factors Affecting the Reproduction and Survival of *Olpidium brassicae* and its transmission of Big Vein Agent to Lettuce. *Phytopathology.* 68(8): 927–935.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A variety of *Lactuca sativa* designated HMX 2557, having the varietal name 'PREMIERE' and having an ATCC accession number 97855, or its progeny, said progeny having resistance to at least three of the diseases selected from the group consisting of lettuce mosaic virus isolate Common, downy mildew pathotype I, corky root bacteria isolate CA1, *Sclerotinia minor*, and big vein disease via infection through *Olpidium brassicae*.

2. A variety of claim 1, wherein the leaf type is green.

3. A variety of claim 1, wherein the average diameter mature head of about 15 cm and weighs about 900 grams.

4. A variety of claim 3 wherein the average mature head is reached in less than about 85 days when grown under optimal soil conditions and daily average temperature of 65° F. in full sun of twelve to thirteen hours duration.

5. A variety of claim 4 wherein the average mature head is reached in less than 70 days.

6. A variety of claim 1 wherein the leaf type is dark green that is between RHS of 146A and 146C.

7. A variety of claim 1 wherein the leaf margin is smooth.

8. A variety of claim 1 wherein the seed color is white.

9. A variety of *Lactuca sativa* designated HMX 2557, having the varietal name 'PREMIERE' and having an ATCC accession number 97855, or its progeny, said progeny having resistance to lettuce mosaic virus isolate Common, resistance to downy mildew pathotype I, resistance to corky root bacteria isolate CA1, resistance to *Sclerotinia minor*, and resistance to big vein disease via infection through *Olpidium brassicae*.

* * * * *